United States Patent
Zeng et al.

(10) Patent No.: US 9,629,791 B2
(45) Date of Patent: Apr. 25, 2017

(54) CATIONIC POLYMER LATEXES AND USES

(75) Inventors: Fanwen Zeng, Belle Mead, NJ (US); Miao Wang, Schwenksville, PA (US)

(73) Assignee: Rohm and Haas Company, Philadelphia, PA (US)

( * ) Notice: Subject to any disclaimer, the term of this patent is extended or adjusted under 35 U.S.C. 154(b) by 229 days.

(21) Appl. No.: 13/988,626

(22) PCT Filed: Dec. 12, 2011

(86) PCT No.: PCT/US2011/064427
§ 371 (c)(1),
(2), (4) Date: May 21, 2013

(87) PCT Pub. No.: WO2012/087636
PCT Pub. Date: Jun. 28, 2012

(65) Prior Publication Data
US 2013/0259812 A1    Oct. 3, 2013

Related U.S. Application Data

(60) Provisional application No. 61/425,016, filed on Dec. 20, 2010.

(51) Int. Cl.
| | |
|---|---|
| *A61K 8/81* | (2006.01) |
| *A61Q 5/00* | (2006.01) |
| *A61Q 19/00* | (2006.01) |
| *C08F 226/02* | (2006.01) |
| *C08F 220/34* | (2006.01) |
| *A61Q 17/04* | (2006.01) |
| *A61Q 1/00* | (2006.01) |
| *A61Q 5/02* | (2006.01) |
| *A61Q 5/12* | (2006.01) |
| *A61Q 19/10* | (2006.01) |
| *A61Q 3/02* | (2006.01) |
| *A61Q 5/06* | (2006.01) |
| *C08L 33/16* | (2006.01) |

(52) U.S. Cl.
CPC .............. *A61K 8/81* (2013.01); *A61K 8/8152* (2013.01); *A61Q 1/00* (2013.01); *A61Q 3/02* (2013.01); *A61Q 5/02* (2013.01); *A61Q 5/06* (2013.01); *A61Q 5/12* (2013.01); *A61Q 17/04* (2013.01); *A61Q 19/00* (2013.01); *A61Q 19/10* (2013.01); *C08F 220/34* (2013.01); *C08F 226/02* (2013.01); *C08L 33/16* (2013.01)

(58) Field of Classification Search
None
See application file for complete search history.

(56) References Cited

U.S. PATENT DOCUMENTS

| | | | |
|---|---|---|---|
| 2,965,594 | A | 12/1960 | Maeder |
| 2,980,657 | A * | 4/1961 | Melamed ..................... 526/307 |
| 3,287,305 | A | 11/1966 | Maeder |
| 3,497,482 | A | 2/1970 | Hwa |
| 3,968,037 | A | 7/1976 | Morgan et al. |
| 4,419,344 | A | 12/1983 | Strasilla et al. |
| 8,192,504 | B2 | 6/2012 | Baxter et al. |
| 2008/0216978 | A1 | 9/2008 | Baxter et al. |
| 2011/0098364 | A1 | 4/2011 | Braun et al. |

FOREIGN PATENT DOCUMENTS

| | | |
|---|---|---|
| EP | 1524279 A1 | 4/2005 |
| EP | 1967546 A1 | 9/2008 |
| JP | 1987262799 A | 11/1987 |
| JP | 1990300298 A | 12/1990 |
| JP | 2004339347 A | 12/2004 |

* cited by examiner

*Primary Examiner* — Tracy Vivlemore
*Assistant Examiner* — Monica Shin
(74) *Attorney, Agent, or Firm* — Edward L. Brant

(57) ABSTRACT

Described are novel polymers and home and personal care compositions incorporating said polymers.

14 Claims, No Drawings

CATIONIC POLYMER LATEXES AND USES

CROSS REFERENCE TO RELATED APPLICATIONS

This application is a 35 USC §371 national phase filing of PCT/US2011/064427 filed Dec. 12, 2011, which claims the benefit of U.S. Application No. 61/425,016, filed Dec. 20, 2010.

FIELD

The present invention relates to new cationic polymer latexes, and uses of the same as opacifiers.

BACKGROUND

Cationic monomers, including Acryloxyethyldimethyl (benzyl) Ammonium Chloride ("ADAMQUAT"), MethacrylolAminopropyl Trimethyl Ammonium Chloride ("MAPTAC"), or Methacryloxyethyldimethyl Ammonium Chloride ("MADQUAT"), are important flocculants.

Moreover, when copolymerized with certain aromatic monomers, cationic polymers may be used to form cationic polymer latexes that have a variety of uses, particularly as opacifiers in relatively low pH home and personal care compositions. Such low pH home and personal care compositions frequently contain betaines, polyquaterniums, or other positively charged ingredients that can cause stability issues with anionic opacifiers, but these stability issues are resolved by certain cationic polymer latex opacifiers. Particularly good cationic polymer latex opacifiers are described in US Pat. App. Pub. 2008/0216978, the entirety of which is incorporated by reference herein.

It should be understood that an opacifier is a material added to give a translucent luster to formulations, said appearance being the result of the refractive index of the material. As visual aesthetic is of great importance to consumers, and many home and personal care compositions contain betaines, polyquaterniums, or other positively charged ingredients, there exists a strong desire in the industry to identify new materials useful as opacifiers.

Therefore, what is needed is new cationic polymers and cationic polymer latexes.

DESCRIPTION

In one embodiment, the present invention provides a cationic latex emulsion containing polymerized units of compounds, including salts, of Formula I:

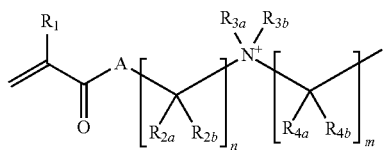

wherein:
A is NH or O;
n is 2-8;
m is 0-18;
$R_1$ is H or —$CH_3$;
$R_{2a}$ and $R_{2b}$, are, independently at each occurrence, H or optionally substituted C1-C6 alkyl;
$R_{3a}$ and $R_{3b}$ are, independently, optionally substituted C1-C6 alkyl, with the proviso that when $R_{3a}$ and $R_{3b}$ are each —$CH_3$, A is O, n is 3, each $R_{2a}$ and $R_{2b}$ are H, then m is greater than 2; and
$R_{4a}$ and $R_{4b}$, are, independently at each occurrence, H or optionally substituted C1-C6 alkyl.

The term "optionally substituted" as used herein means that the groups in question are either unsubstituted or substituted with one or more groups, radicals or moieties, selected from halogen, hydroxy, amino or carboxy. When the groups in question are substituted with more than one substituent, the substituents may be the same or different. In one embodiment, the optional substituent is selected to produce a cosmetically acceptable compound. "Cosmetically acceptable" refers to ingredients typically used in personal care compositions, and is intended to underscore that materials that are toxic, irritating, or unpleasant smelling when present in the amounts typically found in personal care compositions are not contemplated as part of the present invention. In one embodiment, the optional substituent is hydroxy.

"Alkyl" means a saturated monovalent linear or branched aliphatic hydrocarbon radical. Representative examples include, but are not limited to methyl, ethyl, propyl, isopropyl, butyl, isobutyl, tert-butyl, sec-butyl, pentyl, isopentyl, neopentyl, hexyl, isohexyl, and the like.

Salts means that a counter-ion is present, preferably halogen, more preferably $Br^-$, $Cl^-$.

In one embodiment, n is 2-8. In one embodiment, m is 1-3, 4-6, 7-11, or preferably 12-18.

Alternatively, n is 2. In this embodiment, preferably, at least one of the following is also true: m is 12-18, A is O, and/or $R_{3a}$ and $R_{3b}$ are each —$CH_3$.

In one embodiment, at least one of $R_{3a}$ and $R_{3b}$ is —$CH_2OH$, —$CH_2CH_2OH$, or —$CH_2CH(OH)CH_2OH$.

To make the monomer of Formula I, aminoalkyl esters or imides of (meth)acrylic acids may be combined with alkyl halides. As used herein, "(meth)acrylate" means acrylate or methacrylate, and "(meth)acrylic" means acrylic or methacrylic.

In one embodiment, the monomer of Formula I is polymerized to become a repeat unit in a cationic homopolymer or copolymer (said term being used in its broadest sense to include tripolymers, terpolymers, etc.). Said copolymers may have the various types of repeat units arranged randomly, in sequence, in blocks, and other conventional manners. Generally, polymers of the present invention have weight-average molecular weight (Mw) of 1,000 or more.

Suitable monomers to create the copolymer include aromatic monomers, preferably styrene. In some embodiments, styrene or substituted styrene or a mixture thereof is used. Some suitable substituted styrenes are, for example, alkyl-substituted styrenes, halo-substituted styrenes, and alkoxy-substituted styrenes. Some additional suitable aromatic monomers are, for example, (meth)acrylate esters in which the ester group contains an aromatic ring, phenyl(meth)acrylates, vinyl phenyl sulfide, and N-benzyl(meth)acrylamide.

Suitable monomers to create the copolymer also include other cationic monomers, such as acryloyloxyethyl dimethyl (benzyl) ammonium chloride, methacrylolaminopropyl trimethyl ammonium chloride, or methacryloxyethyl trimethyl ammonium chloride. In a preferred embodiment, one of the additional cationic monomers is methacrylol aminopropyl trimethyl ammonium chloride.

Suitable monomers to create the copolymer also include additional monomers include, for example, anionic monomers, lower-alkyl(meth)acrylate esters, higher-aliphatic (meth)acrylate esters, hydroxy-containing monomers such as hydroxy-alkyl (meth)acrylate ester), crosslinking monomers, amides of (meth)acrylic acid, wherein the nitrogen atom of an amide of (meth)acrylic acid may be substituted or unsubstituted, other monomers capable of copolymerizing with cationic monomer and aromatic monomer, and mixtures thereof.

In a preferred embodiment of the present invention, the monomer of Formula I is polymerized and used to form a cationic latex emulsion in any conventional manner, such as that described in US 2008/0216978, the entirety of which is incorporated by reference herein. In one embodiment, the monomer of Formula I is subjected to aqueous emulsion polymerization to form the latex.

A preferred cationic latex emulsion should have a particle size from 150-250 nm and zeta potential greater than 10 mV.

In one embodiment, the present invention provides a method for providing opacity in a personal care composition, comprising including the cationic latex emulsion described above into the personal care composition. A cationic latex emulsion is considered good if it displays excellent opacity while passing formulation stability for formulations containing polyquats.

The personal care composition is preferably a hair care composition (including, for example, shampoos, conditioning shampoos, hair dyes, hair conditioners (leave-on and rinse off), gels, pomades, mousses and hair sprays) or a skin care composition (including, for example, nail coatings, cosmetics, astringents, depilatories, facial make-up formulations, sunscreens and sunblocks, premoistened wipes, hand creams, hand and body soaps, skin cleansers, and hand and body lotions). Personal care adjuvants include certain proteins, synthetic oils, vegetable or animal oils, silicone oils, waxes, resins, gums, humectants, pigments, acidifying or alkalinizing agents, preservatives, dispersants, suspending agents, emollients, (C1-C20) alcohol solvents, sunscreen agents, perfumes, rheology modifiers or thickeners, fragrances, conditioning agents, softeners, antistatic aids, pigments, dyes, tints, colorants, antioxidants, reducing agents and oxidizing agents, film forming materials, stabilizers, neutralizers, preservatives, insecticides, plasticizers, antifoaming agents, leveling aids, excipients, vitamins, natural extracts, proteins, sequestrants, dispersants, antioxidants, suspending agents, and mixtures thereof.

In one embodiment, the present invention provides a method for providing opacity in a home care composition, comprising including the cationic latex emulsion described above into the home care composition. The home care composition may be liquid detergents, hand dishwashing detergents, industrial cleaners, hard surface care products, fabric softeners, machine dishwashing liquids, hand sanitizers, hand treatment products, fragrances, odor neutralizing products. or the like, preferably a dishwashing composition or a laundry composition. Laundry adjuvants include, for example, hydrotropes, builders, cellulose derivatives, dispersants, enzymes, enzyme stabilizing agents, fluorescent whitening agents, bleaching agents, and mixtures thereof.

The amounts and formulation of the various personal care and home care compositions are readily apparent to those of ordinary skill in the art.

EXAMPLES

The following examples are for illustrative purposes only and are not intended to limit the scope of the present invention.

Example 1

Preparation of Hydrophobic Cationic Monomer, N-methacryloyloxyethyl-N-hexadecyl-N,N-dimethylammonium Bromide (Monomer Quat-16)

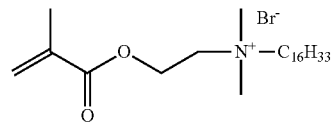

Examples of cationic monomers of the present invention include N-methacryloyloxyethyl-N-hexadecyl-N,N-dimethylammonium chloride. To prepare the same, to a 3 neck round bottom flask equipped with a stirrer, thermocouple, and condenser 78.61 g (0.51 mol) 2-(dimethylamino) ethyl methacrylate, 152.67 g (0.5 mol) 1-bromohexadecane, 462.56 g of acetone and 0.05 g hydroquinone are added. The solution is heated to 40° C. and held at temperature for 20 hours. After 20 hours, the solution is poured into a 1 L neck flask. The solvent is removed by roto-evaporation under reduced pressure. The resulting monomer, abbreviated as Quat-16, was re-crystallized from dry ethyl acetate.

Example 2

Examples of cationic polymer latexes of the present invention are listed in TABLE 1:

TABLE 1

| Example | | Particle Size ("PS") |
|---|---|---|
| P1 | 81 STY/17 HEMA/1 MAPTAC/1 Quat-16 | 165 |
| P2 | 80 STY/17 HEMA/1 MAPTAC/2 Quat-16 | 189 |
| P3 | 81 STY/17 HEMA/2 Quat-16 | 158 |
| P4 | 82 STY/17 HEMA/1 Quat-16 | 207 |

STY = Styrene
HEMA = 2-hydroxyethyl methacrylate
MAPTAC = 3-(methacrylolamino)propyl]-trimethylammonium chloride, supplied by Evonik To a 1-liter round-bottom flask equipped with an overhead stirrer, thermocouple, condenser and inlets for the addition of monomer and initiators is charged 259 grams of deionized water, 1.5 grams of a 70% TERGITOL™ 15-S-40 surfactant and 10 grams of 50% CAVASOL™ W7 M TL (cyclodextrin from Wacker Fine Chemicals). The flask is stirred and heated to 82° C.

A monomer emulsion is prepared by charging 88.4 grams of deionized water and 11 grams of 70% TERGITOL™ 15-S-40 surfactant to an appropriate container and set to stir. After the surfactant is incorporated into the water, 202 grams of styrene are added slowly to the stirring mixture. Then, 42.5 grams of HEMA is added to the mixture. A co-feed catalyst solution is also prepared by charging 0.58 grams of VAZO™ 56 (2,2'-azobis(2-methylpropionamide)dihydrochloride from E. I. du Pont de Nemours and Company) and 30 grams of deionized water.

At reaction temperature of 82° C., 34.8 grams of the above prepared monomer emulsion is charged to the kettle with a 20 gram deionized water rinse, followed by 5 grams of 50% MAPTAC solution and an initiator solution of 0.45 grams VAZO™ 56 and 10 grams water. The reaction temperature bottoms out at approximately 77° C., and the reaction is then held for 20 minutes. After the 20 minute hold, with the temperature is allowed to increase to 82° C.

During the hold, 2.5 grams of monomer Quat-16 is added into the monomer emulsion with mixing. At the end of hold, with the temperature allowed to increase to 82° C., the monomer emulsion co-feed is begun at a rate of 3.83 grams per minute for 90 minutes. Simultaneously the catalyst co-feed is begun at a rate of 0.28 grams per minute for 110 minutes. At the completion of the monomer emulsion co-feed, 10 grams of deionized water is added as a rinse. The reaction is then held for 30 minutes at 82° C. After the 30 minute hold is completed, the chaser catalyst mixture is added to the kettle for 60 minutes. At the completion of the chaser feed, the reaction is held for 20 additional minutes. After the hold is completed, the reaction is cooled to room temperature and then filtered through a 100 mesh bag and then through a 325 mesh bag.

Using substantially the above protocol, the cationic polymer latexes were made. Upon testing, P1 had the following characteristics. Solids is the weight of solid material left when the latex is evaporated to dryness, as a percentage of the total weight of latex. Grit is the amount of material retained in the mesh bags. Mean particle size was measured with a Brookhaven Instruments Corp. BI-90 device. Residual Monomer amounts were measured by head space gas chromatography.

| | |
|---|---|
| Solids: | 35.6% |
| Grit: | <100 ppm |
| Mean Particle Size: | 165 nm |
| Residue Styrene: | 54 ppm |

Example 3 (Comparative)

Examples of comparative cationic polymer latexes are listed in TABLE 2:

TABLE 2

| Example | | PS |
|---|---|---|
| Comparative polymer A (no MAPTAC) | 83 STY/17 HEMA | 244 |
| Comparative polymer B (low MAPTAC) | 82 STY/17.5 HEMA/0.5 MAPTAC/ 0.5 DVB | 165 |
| Comparative polymer C (high MAPTAC) | 82 STY/17 HEMA/3 MAPTAC | 135 |

DVB = divinylbenzene

Using a protocol substantially similar to Example 2, the above comparative cationic polymer latexes were prepared.

The resulting latex A had the following characteristics.

| | |
|---|---|
| Solids: | 35.5% |
| Grit: | 4000 ppm |
| Mean Particle Size: | 278 nm |
| Residual Styrene: | 244 ppm |

The resulting latex B had the following characteristics.

| | |
|---|---|
| Solids: | 35.6% |
| Grit: | <100 ppm |
| Mean Particle Size: | 165 nm |

Example 4

Zeta potential was measured at approximately 5 mM KCl at 25° C. using Malvern Zetasizer™ instrument. Dilutions of each latex were varied so as to give dilute solutions with good light scattering response on the instrument. pH adjustments were made using dilute HCl or dilute NaOH. All solutions were roughly equilibrated to pH then allowed to stand for approximately 30 minutes. Solutions were then adjusted to final pH and allowed to stand a minimum of 30 minutes prior to analysis. Concentrations studied were approximately 0.02 to 0.15 mg polymer solids per milliliter of diluent. Reported measurements in the table below are the average of several measurements on that single solution studied.

TABLE 3

| Example | ZP (mV) |
|---|---|
| comparative example A | 17.0 |
| comparative example B | NM |
| comparative example C | 35.0 |
| P1 | 17.4 |
| P2 | 17.3 |
| P3 | 13.0 |
| P4 | 13.0 |

NM: not measured

Example 5

To test formulation stability for formulations containing polyquats, three base compositions were prepared:

Bodywash Formulation Based on Polyquaternium 7 (PQ-7)

TABLE 4A

| ingredient | Trade Name Material | Low Level | High Level | Order of addition |
|---|---|---|---|---|
| water | | qs. To 100 | qs. To 100 | 1 |
| sodium laureth sulfate (SLES) | Empicol ESB70/ A@ (70% AI) | 5 | 12 | 2 |
| cocamidopropyl betaine (CAPB) | Empigen BSFA (30% AI) | 1 | 4 | 3 |
| Polyquaternium 7 (PQ-7) | Salcare Super 7 | 0.2 | 0.5 | 4 |
| citric acid or sodium hydroxide | | q.s. to pH 4.5 | q.s. to pH 7.0 | 5 |
| preservatives | Neolone PE | 0.55 | 0.55 | 6 |
| sodium chloride | | 0.8 | 0.8 | 7 |
| Opacifier | | 1 as is | 1 as is | 8 |
| Water | | 4 | 4 | 9 |

1. Disperse SLES in water with proper mixing, followed by CAPB. Add PQ-7 to surfactants solution. Adjust pH to target using citric acid or sodium hydroxide.

2. Add preservative, and sodium chloride to the formulation.

3. Premix Opacifier with water, then add it to the final formulation.

Bodywash Formulation Based on Polyquaternium Guar HPTC

TABLE 4B

| ingredient | Trade Name Material | Low Level | High Level | Order of addition |
|---|---|---|---|---|
| water | | qs. To 100 | qs. To 100 | 1 |
| Guar HPTC | Jaguar C-13S | 0.15 | 0.4 | 2 |
| citric acid | | qs to pH 3 | | 3 |
| CAPB | Empigen BSFA | 1.5 | 3.5 | 4 |
| SLES | Empicol ESB70/A@ | 11 | 11 | 5 |
| citric acid or sodium hydroxide | | q.s. to pH 4.5 | q.s. to pH 7.0 | 6 |
| Neolone PE | | 0.55 | 0.55 | 7 |
| sodium chloride | | 1 | 1 | 8 |
| Opacifier | | 1 as is | 1 as is | 9 |
| Water | | 4 | 4 | 10 |

1. Disperse Guar HPTC in water with proper mixing, after well hydrated, add CAPB, followed by SLES. Adjust pH to target using citric acid or sodium hydroxide.

2. Add preservative, and sodium chloride to the formulation.

3. Premix Opacifier with water, then add it to the final formulation

Bodywash Formulation Based on Polyquaternium 10 (PQ-10)

TABLE 4C

| Ingredient | Trade Name Material | Low Level | High Level | Order of addition |
|---|---|---|---|---|
| Water | | qs. To 100 | qs. To 100 | 1 |
| Polyquaternium 10 | UCARE Polymer LK | 0.2 | 0.5 | 2 |
| Citric acid | | qs to pH 3 | | 3 |
| CAPB | Empigen BSFA | 1 | 4 | 4 |
| SLES | Empicol ESB70/A@ | 5 | 12 | 5 |
| Citric acid or sodium hydroxide | | q.s. to pH 4.5 | q.s. to pH 7.0 | 6 |
| Neolone PE | | 0.55 | 0.55 | 7 |
| Sodium chloride | | 0.8 | 0.8 | 8 |
| Opacifier | | 1 as is | 1 as is | 9 |
| Water | | 4 | 4 | 10 |

1. Disperse PQ-10 in water with proper mixing, after well hydrated, add CAPB, followed by SLES. Adjust pH to target using citric acid or sodium hydroxide.

2. Add preservative, and sodium chloride to the formulation.

3. Premix Opacifier with water, then add it to the final formulation.

Example 6

Heat-age stability and opacity of bodywash formulations containing polyquatemium and cationic latex are summarized in TABLE 5.

TABLE 5

| Polymer example | Testing temp. (° C.) | PQ-7 Opac. | PQ-7 Form. stability | PQ-10 Opac. | PQ-10 Form. stability | Guar Opac. | Guar Form. stability |
|---|---|---|---|---|---|---|---|
| Comp. polymer A | 20 | O | E | LO | XP | O | P |
| | 40 | O | XP | LO | XP | O | XP |
| Comp. polymer B | 20 | O | E | O | XP | O | P |
| | 40 | O | E | O | P | O | P |
| Comp. polymer C | 20 | WO | E | WO | E | WO | E |
| | 40 | WO | E | WO | E | WO | E |
| P1 | 20 | MO | E | O | F | MO | E |
| | 40 | MO | E | O | F | MO | E |
| P2 | 20 | O | E | O | XP | MO | P |
| | 40 | O | E | O | P | MO | F |
| P3 | 20 | MO | E | O | F | MO | E |
| | 40 | MO | E | O | F | MO | XP |
| P4 | 20 | MO | E | O | XP | MO | P |
| | 40 | MO | E | O | P | MO | F |

Formulation heat-age stability of each formulation was assessed using the following rating system. Backscattering over time as a function of position (top to bottom) within each sample was determined using a Turbiscan™ instrument, model TLabExpert from Formulaction Company. Changes in backscattering that were uniform from top to bottom were considered flocculation. Changes in backscattering that varied as a function of position in the sample were considered sedimentation or creaming. Samples were observed for one month (or less if they showed poor stability). At the end of the observation period the following rating scale was used:

| Observation | Rating |
|---|---|
| severe flocculation and/or sedimentation or creaming | XP = extremely poor |
| slight flocculation and/or sedimentation or creaming | P = poor |
| very slight flocculation and/or sedimentation or creaming | F = fair |
| miniscule flocculation and/or sedimentation or creaming | G = good |
| no flocculation and/or sedimentation or creaming | E = excellent |

Each stability test was conducted at two different temperatures, 20 and 40° C. A fair stability at 40° C. for 6-8 weeks can be correlated to a 1 year stability at RT. Opacity of formulations, i.e., the ability of each polymer latex to provide opacity was tested. Each bodywash formulation contained 1% cationic polymer latex as supplied based on the total weight of the formulation. The appearance of the bodywash formulation was either ranked by either back scattering measurement or eye observation. The ranking scale was as follows, from most opaque to least opaque:

MO (most opaque, very good),
O (opaque, good),
LO (blue-gray, less opaque),
WO (translucent, poor, worst opaque).

The inventive compositions had a desirable balance of opacity and stability as compared to the comparatives, for example, sample C, which has poor opacity even though the formulation stability is excellent.

Of the inventive polymers, P1 and P2, polymers with a combination of two cationic monomers have both opacity and stability, performed better than polymers with only Quat-16.

It is understood that the present invention is not limited to the embodiments specifically disclosed and exemplified herein. Various modifications of the invention will be apparent to those skilled in the art. Such changes and modifications may be made without departing from the scope of the appended claims. Moreover, each recited range includes all combinations and subcombinations of ranges, as well as specific numerals contained therein. Additionally, the disclosures of each patent, patent application, and publication cited or described in this document are hereby incorporated herein by reference, in their entireties.

The invention claimed is:

1. A composition comprising (i) a polyquaternium, and (ii) a cationic polymer latex emulsion containing polymerized units of:
   (a) 1 to 2 weight %, based on the total weight of the polymer, of a compound, including a salt, of Formula I:

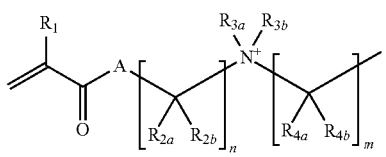

wherein:
   A is O;
   n is 2-3;
   m is 12-18;
   $R_1$ is H or —$CH_3$;
   $R_{2a}$ and $R_{2b}$, are, independently at each occurrence, H;
   $R_{3a}$ and $R_{3b}$ are, independently, —$CH_3$; and
   $R_{4a}$ and $R_{4b}$, are, independently at each occurrence, H;
   (b) an aromatic monomer; and
   (c) a monomer that is neither cationic nor aromatic.

2. The composition of claim 1, wherein n is 3.

3. The composition of claim 1, wherein the aromatic monomer is selected from the group consisting of styrene, substituted styrene, and mixtures thereof.

4. The composition of claim 1, further comprising polymerized units of at least one other cationic monomer.

5. The composition of claim 1, wherein the monomer that is neither cationic nor aromatic comprises 2-hydroxyethyl methacrylate.

6. A method for providing opacity in a personal care composition, comprising including the composition of claim 1 into the personal care composition.

7. A hair care composition containing the composition of claim 1.

8. A skin care composition containing the composition of claim 1.

9. A method for providing opacity in a home care composition, comprising including the composition of claim 1 into the home care composition.

10. The composition of claim 3, wherein the aromatic monomer comprises styrene.

11. A composition comprising (i) a polyquaternium, and (ii) a cationic polymer latex emulsion containing polymerized units derived from:
    (a) 1 to 2 weight %, based on the total weight of the polymer, of a compound, including a salt, of Formula I:

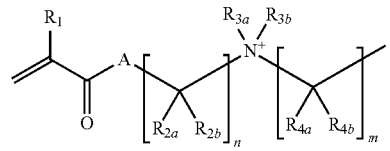

wherein:
    A is O;
    n is 2-3;
    m is 12-18;
    $R_1$ is H or —$CH_3$;
    $R_{2a}$ and $R_{2b}$, are, independently at each occurrence, H;
    $R_{3a}$ and $R_{3b}$ are, independently, —$CH_3$; and
    $R_{4a}$ and $R_{4b}$, are, independently at each occurrence, H;
    (b) 80 to 82 weight %, based on the total weight of the polymer, of an aromatic monomer; and
    (c) 16 to 18 weight %, based on the total weight of the polymer, of a monomer that is neither cationic nor aromatic.

12. The composition of claim 11, wherein the aromatic monomer is selected from the group consisting of styrene, substituted styrene, and mixtures thereof.

13. The composition of claim 11, wherein the monomer that is neither cationic nor aromatic comprises 2-hydroxyethyl methacrylate.

14. The composition of claim 12, wherein the monomer that is neither cationic nor aromatic comprises 2-hydroxyethyl methacrylate.

* * * * *